United States Patent [19]

Bettarini et al.

[11] Patent Number: 4,460,606
[45] Date of Patent: Jul. 17, 1984

[54] METHOD FOR FIGHTING INFESTATIONS BY ANTS

[75] Inventors: Franco Bettarini, Novara; Pietro Massardo, Milan; Paolo Piccardi, Milan; Angelo Longoni, Milan, all of Italy

[73] Assignee: Montedison S.p.A., Milan, Italy

[21] Appl. No.: 379,177

[22] Filed: May 17, 1982

Related U.S. Application Data

[63] Continuation-in-part of Ser. No. 198,488, Oct. 20, 1980, Pat. No. 4,356,329.

[30] Foreign Application Priority Data

Jun. 21, 1978 [IT] Italy .......................................... 24794
Mar. 5, 1979 [IT] Italy .......................................... 20734

[51] Int. Cl.$^3$ ............................................ A01N 31/14
[52] U.S. Cl. ..................................................... 424/341
[58] Field of Search ........................................ 424/341

[56] References Cited

U.S. PATENT DOCUMENTS

| 3,322,813 | 5/1967 | Seki et al. ............................ 568/649 |
| 3,379,755 | 4/1968 | Schultz ................................ 568/649 |
| 3,816,541 | 6/1974 | Mihailovski et al. ................ 568/649 |
| 4,061,683 | 12/1977 | Karrer .................................. 568/637 |
| 4,126,623 | 11/1978 | Piccardi et al. .............. 260/340.5 R |
| 4,141,921 | 2/1979 | Karrer .................................. 568/637 |
| 4,153,731 | 5/1979 | Karrer .................................. 568/637 |
| 4,356,329 | 10/1982 | Bettarini et al. ................... 568/637 |

FOREIGN PATENT DOCUMENTS 877164 12/1979 Belgium .

Primary Examiner—Allen J. Robinson

[57] ABSTRACT

A method for fighting infestations by ants is disclosed. It consists in using 1-[(5-chloro-pent-4-inyl)-oxy]-4-phenoxy-benzene either as such or as an active ingredient of compositions or poisoned baits.

The present invention concerns a method for fighting infestations by ants and, more particularly, it relates to a fighting method that consists in using, for the purpose, the compound 1-[(5-chloro-pent-4-inyl)-oxy]-4-phenoxy-benzene either as such or in the form of suitable formulations.

11 Claims, No Drawings

METHOD FOR FIGHTING INFESTATIONS BY ANTS

BACKGROUND OF THE INVENTION

This application is a continuation-in-part of our application Ser. No. 198,488 filed Oct. 20, 1980, now U.S. Pat. No. 4,356,329.

The noxious species of ants diffused in all parts of the world are quite numerous and the damages they inflict are found in various fields. For instance, in the agricultural field they may prove harmful both by attacking cultivations or foodstuffs, as well as by rendering the fields intended for cultivations or as pastures unusable.

Other kinds of equally heavy damages will be found in the civil area, because of attacks on wooden buildings and structures, and in the veterinary and medical areas by bites and punctures to cattle as well as humans.

The ant species considered most noxious belong mainly to the following genera: Pheidale, Aphaenogaster, Messar, Oecophylla, Macronischoide, Camponotus, Crematogaster, Iridomyrnex, Atta, Acromyrnex and Solenopsis.

One of the sectors in which there have recently been observed ever-increasing damages and considerable difficulties in controlling such infestations is that of the infestations by ants of the Solenopsis genus in a number of southern states in the United States of America.

It has been calculated that, in the USA, the ants of the Solenopsis genus (called "fire-ants") infest with their ant hills (nests), up to 250 per hectare, and render unusable fields having a total surface of about 80 millions of hectares.

To this type of damages there must be added the losses in cattle killed by the poisonous bite of these insects as well as the serious danger for people living in the neighborhood of infested places or for people frequenting such places.

As a matter of fact, there have been reported quite a number of cases where people had been attacked by such ants and had then died because of a high sensitivity to the poison injected by their bite.

Earlier, the fight against Solenopsis ants in the USA was carried out using a compound called Mirex, a polycyclic perchlorinated hydrocarbon.

In spite of the good results obtained with that compound, the same was banned when it was discovered that it left residues in human milk and when it was evidenced that it is cancerogenous and teratogenous. Therefore, because of the still growing diffusion of the infestation, it is necessary to find new active products that, at the same time, are harmless for humans and for the environment.

In Belgian Pat. No. 877,164, assigned to Montedison S.p.A., there are described a number of compounds endowed with a juvenile hormonic activity on noxious insects and thus usable in the agrarian and domestic spheres in the fight against insect infestations.

We have now found that among the compounds disclosed in said Belgian patent, the compound 1-[(5-chloro-pent-4-inyl)oxy]-4-phenoxy-benzene of the formula:

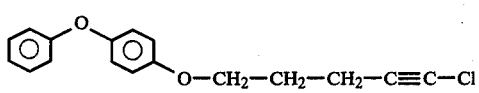
(I)

(hereinafter "compound I") exhibits an extremely high activity against ants. Since compound I is moreover also endowed with a very low toxicity towards warm-blooded animals (at the dose of 3,000 mg/kg no mortality occurred in the acute toxicity tests on rats), and the compound does not appear to be mutagenous in the standard tests that were conducted, it is suitable for use in the fight against ant infestations both in the agricultural field and in environments frequented by humans and by livestock.

Thus, one object of this invention is to provide a method for combatting ant infestations, which method consists in spreading over the infested places an effective amount of compound I, either as such or in the form of suitable compositions or poisoned baits.

Another object of this invention is to provide compositions that are suitable for fighting ant infestations and that contain compound I as an active principle, along with inert vehicles and, optionally, other suitable additives.

In the fight against ants, it is often necessary that the active compound be put into contact also with the larvae of the insects. For this purpose, it proves effective to prepare poisoned baits that nevertheless are desired by the ants, such baits being distributed in the neighborhood of the ant nests so that the worker-ants will introduce the poisoned baits into the nest for nourishing the larvae. Compound I proves also suitable for the preparation of such poisoned baits, and thus, a still further object of this invention is to provide baits containing Compound I diluted in nourishing substances that are appetizing for the ants, and optionally other additives.

In the method of combatting the ants according to this invention, in view of the necessity to kill also the ant-larvae in order to eradicate the infestation, it is preferable to use the product in the form of suitable compositions or poisoned baits.

According to the normal formulating practice, the compound of formula I is used as active ingredient in compositions in the form of a liquid concentrate, a wettable powder or a granular formulate.

In practice, the compositions are then distributed near the ant nests or directly inside the same.

This latter form of application is made possible by the fact that the nests of the ants in general are easily located.

In the above-mentioned compositions, besides compound I as an active principle, there may be present the normal inert carriers or additives used in pesticide formulations such as, for instance, liquid or solid vehicles, surfactants, wetting agents, dispersants, antioxidants, etc.

The application of compound I in the form of poisoned baits in general represents the most effective and efficient method of application because, as mentioned above, it is necessary to kill, also, the ant larvae that are deep inside the ant hill. Since the larvae are fed by the worker-ants which gather the nourishment outside the nest, the poisoned baits represent an optimal vehicle for allowing the active compound to reach the larvae in a capillary way.

A necessary condition for an active compound to be used in this type of treatment is that the compound shall possess a delayed action and not be repellant to the ants. Compound I has these characteristics.

The preparation of the poisoned baits is carried out according to conventional formulating techniques. Thus, for instance, the active compound will be incorporated in either liquid or semi-fluid edible substances such as honey, treacle, vegetable oils, proteic lisates, etc., or it may be dissolved in suitable vehicles, including those of alimentary origin, and sprayed on solid edible material such as lyophilized liver, ground cereals, etc.

In general, the bait consists of edible material of proteic, oily or sugary source, besides a quantity of about 0.1%–5% by weight of active substance and, optionally other suitable additives.

For practical applications of the method for combatting ant infestations according to the invention, the quantity of active substance (compound I) to be distributed, varies according to several factors. Among these may be listed the type and degree of infestation, the place of infestation, the composition used and the corresponding application means available, and climatic and environmental factors.

In general, considering the high activity of compound I, it is sufficient to use an amount of active substance comprised between 1 and 200 g/ha (preferably between 10 and 20 g/ha) for field applications or about 0.50–50 mg per nest.

In the case of other types of applications, such as the protection of materials and foodstuffs, there will be used the amounts found to be effective for that particular application, also depending on environmental conditions.

Compound I is found to be active, also, against infestations by termites. Considering the known behavioral, social-organizational and habitat analogies, and thus the analogies between the damages caused by ants and termites, the method for fighting ant infestations and the compositions and baits that are objects of the present invention, may be extended, without substantial variations, to the fight against termite infestations.

The following examples illustrate the invention in even more detail, but are not intended to be limiting.

EXAMPLE 1

This example describes a field-test under natural conditions of ant infestation by fire ants of the Solenopsis genus, carried out in the State of Mississippi (USA) in June 1981, by the United States Department of Agriculture, using compound I supplied by Montedison S.p.A., Milan, Italy. (This relatively large scale field-test had been preceded by a small scale laboratory test in the summer of 1980 by the U.S.D.A. using compound I also supplied by Montedion). On a permanent pasture not open to cattle were selected three plots of about 2 hectars each. In each of these plots were singled out five further sub-plots of 0.1 ha, in which to observe the activity of the ants before and after treatment.

There were then prepared a number of baits consisting of pregel defatted corn grits (70%), once-refined soybean oil (28 or 29%) and compound I (2 or 1%).

The baits were prepared by incorporating compound I in the soybean oil, and this solution was then sprayed on the corn grits maintained under stirring in a mixer. The baits were applied by a distributor for granular formulates, mounted on a tractor.

The bait with 1% of active ingredients (compound I) was applied to a plot at the rate of 1.126 Kg/ha (corresponding to a dose of 11.27 g/ha of active ingredient) while the 2% bait was applied to a second plot at the rate of 1.014 kg/ha (corresponding to a dose of 20.28 g/ha of active ingredient). The third plot was left untreated and served as a control.

The evaluation of the effectiveness of the treatment was made by observing the activity of the ants before and after the treatment.

Before the treatment, the area of each plot was examined and the number of ant nests were counted, whereupon to each nest there was assigned an index (nest index) based on the estimated number of worker-ants and on the presence or absence of immature workers (larvae) as indicated in the following Table I.

TABLE I

| Number of worker-ants | Nest Index | |
|---|---|---|
| | Absence of immature worker-ants | Presence of immature worker-ants |
| <100 | 1 | 6 |
| 100–1,000 | 2 | 7 |
| 1,000–10,000 | 3 | 8 |
| 10,000–50,000 | 4 | 9 |
| >50,000 | 5 | 10 |

Thereafter, a "population index" was determined for each plot by multiplying the number of ant nests, with a certain "nest index", by the index itself and by then summing the totals for the plot.

The comparison between the number of active nests and the population index before and after the treatment provides the means for determining the effectiveness of the treatment.

The following Table II shows the results obtained 13 weeks after the date of treatment.

TABLE II

Effectiveness of compound I in a field-test against ants of the Solenopsis genus

| | | Before treatment | | | 13 weeks after treatment[d] | | | Percentual variation | | |
|---|---|---|---|---|---|---|---|---|---|---|
| Plot No. | Sub-plot No. | Number active nests | Population index | Average index of nests | Number active nests | Population index | Average index of nests | Active nests | Population Index | Average index of nests |
| 1[a] | 1 | 10 | 95 | 9.50 | 1 | 3 | 3.00 | −88.6 | −96.4 | −68.0 |
| | 2 | 10 | 90 | 9.00 | 1 | 1 | 1.00 | −88.6 | −98.8 | −88.4 |
| | 3 | 9 | 82 | 9.11 | 2 | 4 | 2.00 | −74.7 | −94.5 | −77.6 |
| | 4 | 8 | 69 | 8.63 | 0 | 0 | 0 | −100 | −100 | −100 |
| | 5 | 9 | 89 | 9.89 | 0 | 0 | 0 | −100 | −100 | −100 |
| | Total | 46 | 425 | 9.24 | 4 | 8 | 2.0 | −90.1 | −97.9 | −77.9 |
| 2[b] | 6 | 10 | 90 | 9.00 | 2 | 2 | 1.00 | −77.2 | −97.5 | −88.4 |
| | 7 | 10 | 93 | 9.30 | 1 | 1 | 1.00 | −88.6 | −98.8 | −88.7 |
| | 8 | 4 | 31 | 7.75 | 1 | 4 | 4.00 | −71.6 | −85.4 | −48.1 |
| | 9 | 8 | 71 | 8.88 | 2 | 3 | 1.50 | −71.6 | −95.2 | −82.6 |
| | 10 | 10 | 96 | 9.60 | 4 | 7 | 1.75 | −54.5 | −91.7 | −81.3 |
| | Total | 42 | 381 | 9.07 | 10 | 17 | 1.70 | −72.9 | −94.9 | −80.8 |
| 3[c] | 11 | 9 | 83 | 9.22 | 8 | 68 | 8.50 | −11.1 | −18.1 | −7.8 |
| | 12 | 14 | 130 | 9.29 | 8 | 72 | 9.00 | −42.9 | −44.6 | −3.1 |

TABLE II-continued

Effectiveness of compound I in a field-test against ants of the Solenopsis genus

| Plot No. | Sub-plot No. | Before treatment | | | 13 weeks after treatment[d] | | | Percentual variation | | |
|---|---|---|---|---|---|---|---|---|---|---|
| | | Number active nests | Population index | Average index of nests | Number active nests | Population index | Average index of nests | Active nests | Population Index | Average index of nests |
| | 13 | 17 | 146 | 8.59 | 18 | 170 | 9.44 | +5.9 | +16.4 | +9.9 |
| | 14 | 11 | 88 | 8.00 | 9 | 60 | 6.67 | −18.2 | −31.8 | −16.6 |
| | 15 | 7 | 52 | 7.43 | 8 | 71 | 8.88 | +14.3 | +36.5 | +19.5 |
| | Total | 58 | 499 | 8.60 | 51 | 441 | 8.65 | 0(−12.1)[e] | 0(−11.6)[e] | 0(+0.6)[e] |

Notes to Table II:
[a]plot treated with baits containing 1% by weight of compound I at a dose of 11.27 g/ha a.i.;
[b]plot treated with baits containing 2% by weight of compound I at a dose of 20.28 g/ha a.i.;
[c]untreated plot used as a control;
[d]data corrected for the variations of the control according to Abbott's formula;
[e]the data between brackets indicate the percentual variation of the control before correction.

EXAMPLE 2

The activity of compound I was determined in a test of a practical character, carried out towards the end of May 1979, in the province of Latina (Italy) on ants belonging to the *Iridomyrnex humilis* species, a species very diffused in Italy and whose harmfulness may often be very high.

There were singled out in one field, and marked for experimental purposes, 6 ant hills each inhabited by several thousands of individuals, said ant hills being located at a suitable distance from each other.

There was then prepared a sugary solution having the following composition:

| white sugar | 1 kg. |
|---|---|
| water | 1 lt. |
| sodium benzoate | 1.7 g |
| tartaric acid | 1.2 g |

A suitably shaped vessel containing the sugary solution and that allowed the feeding of the ants but not of bees, was placed near each of three ant hills.

Identical vessels, one for each ant hill, were placed near the other three ant hills, the sugary solution contained in them having been additioned with 2% by weight of compound I previously dissolved in a little acetone.

Six weeks after administering the sugary solution, the ant hills were examined and the level of population present in each of them was assessed.

The ant hills kept as a control and which had been administered the sugary solution not containing compound I, appeared densely populated, while the ant hills which had been fed on a sugary solution additioned with compound I contained only a few tens of individuals and seemed to be undergoing extinction since the absence of larvae was observed.

The procedures and results of the tests are summarized in the following Table III:

TABLE III

| Ant hill No. | Nourishment | Level of population before treatment (approximate No. of individuals) | Level of population 6 weeks after treatment (approximate No. of individuals) |
|---|---|---|---|
| 1 | sugary solution | 2,000–5,000 | 2,000–5,000 |
| 2 | sugary solution | 2,000–5,000 | 2,000–5,000 |
| 3 | sugary solution | 2,000–5,000 | 2,000–5,000 |
| 4 | sug. sol. + 2% comp. I | 2,000–5,000 | ≦150 |
| 5 | sug. sol. + 2% comp. I | 2,000–5,000 | 100 ca. |
| 6 | sug. sol. + 2% comp. I | 2,000–5,000 | <50 |

What is claimed is:

1. A method for combating infestations by ants, consisting in distributing in the infested places an effective amount of the compound of formula:

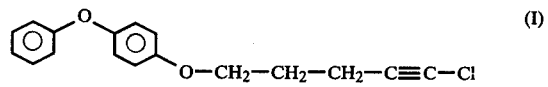

(I)

either alone or in the form of a composition.

2. The method for combating ant infestations according to claim 1 in which the ants are of the genus Solenopsis.

3. The method for combating ant infestations according to claim 1 in which the ants are fire ants.

4. The method of claim 1 in the form of a composition and the ants are ants of the genus Solenopsis.

5. The method of claim 4, in which the composition is in the form of a poisoned bait.

6. The method of claim 5, in which the poisoned bait further contains a surfactant or an antioxidant.

7. The method of claim 1, in the form of a composition and the ants are fire ants.

8. A composition for combating infestations by ants containing (a) an effective amount of the compound of formula:

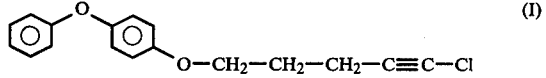

(I)

as active ingredient, and (b) an inert carrier.

9. A composition according to claim 8, which further contains a surfactant or an antioxidant.

10. A composition according to claim 8 in the form of a poisoned bait.

11. A composition according to claim 9, in the form of a poisoned bait.